(12) United States Patent
Miller et al.

(10) Patent No.: US 10,045,928 B2
(45) Date of Patent: Aug. 14, 2018

(54) NON-AQUEOUS PEELABLE NAIL POLISH

(71) Applicant: Mycone Dental Supply Company, Inc., Gibbstown, NJ (US)

(72) Inventors: Timothy M. Miller, Phoenixville, PA (US); Robert R. Raney, Newtown Square, PA (US)

(73) Assignee: Mycone Dental Supply Company, Inc., Gibbstown, NJ (US)

( * ) Notice: Subject to any disclaimer, the term of this patent is extended or adjusted under 35 U.S.C. 154(b) by 51 days.

(21) Appl. No.: 15/279,861

(22) Filed: Sep. 29, 2016

(65) Prior Publication Data

US 2018/0085300 A1  Mar. 29, 2018

(51) Int. Cl.
| | |
|---|---|
| *A61Q 3/02* | (2006.01) |
| *A61K 8/73* | (2006.01) |
| *A61K 8/81* | (2006.01) |
| *A61Q 3/00* | (2006.01) |

(52) U.S. Cl.
CPC ............ *A61K 8/731* (2013.01); *A61K 8/8129* (2013.01); *A61K 8/8135* (2013.01); *A61Q 3/00* (2013.01); *A61Q 3/02* (2013.01); *A61K 2800/30* (2013.01); *A61K 2800/31* (2013.01)

(58) Field of Classification Search
CPC ...................................................... A61Q 3/02
See application file for complete search history.

(56) References Cited

U.S. PATENT DOCUMENTS

| | | |
|---|---|---|
| 2,764,168 A | 9/1956 | Herz |
| 4,126,144 A | 11/1978 | Duarte |
| 4,146,511 A | 3/1979 | Moriya et al. |
| 4,166,110 A | 8/1979 | Isobe et al. |
| 4,283,324 A | 8/1981 | Duffy |
| 4,402,935 A | 9/1983 | Gordon et al. |
| 5,830,443 A | 11/1998 | Lee |
| 6,964,989 B1 | 11/2005 | Fang et al. |
| 7,645,444 B2 | 1/2010 | Malnou et al. |
| 8,263,231 B2 | 9/2012 | Mesa |
| 9,211,242 B2 | 12/2015 | Renard et al. |
| 2003/0175225 A1* | 9/2003 | Leacock ............ A61K 8/29 424/61 |
| 2006/0084585 A1 | 4/2006 | Lin |

FOREIGN PATENT DOCUMENTS

| | | | |
|---|---|---|---|
| FR | 2379280 | 9/1978 | |
| FR | 2819176 | 7/2002 | |
| GB | 551619 A * | 3/1943 | ........... A43D 11/003 |
| JP | 2001149136 | 6/2001 | |
| JP | 2001270810 | 10/2001 | |
| WO | WO-9955291 A1 * | 11/1999 | ............. A61K 8/731 |
| WO | WO-2015101364 A2 * | 7/2015 | ................ A61K 8/34 |
| WO | WO-2017153373 A1 * | 9/2017 | ................ A61K 8/25 |

OTHER PUBLICATIONS

Google Machine Translation, WO20171533731, accessed at https://patents.google.com/patent/WO2017153373A1/en, Mar. 31, 2018 (Year: 2017).*
"Tensile modulus", Polymer Science Dictionary, 3rd ed. Alger, Ed., Springer Science Business Media, Dordrecht, p. 887 (Year: 2017).*
International Search Report and Written Opinion in International Application No. PCT/US2017/049708, dated Nov. 7, 2017, 13 pages.

* cited by examiner

*Primary Examiner* — Robert A Wax
*Assistant Examiner* — Melissa S Mercier
(74) *Attorney, Agent, or Firm* — Fish & Richardson P.C.

(57) ABSTRACT

A non-aqueous nail polish consisting of: (a) a film-forming resin selected from the group consisting of vinyl acetate polymers and copolymers, vinyl alcohol polymers and copolymers, vinyl chloride polymers and copolymers, no greater than 5% by weight, based upon the weight of the polish, cellulosic polymers, and combinations thereof; (b) one or more organic solvents; and (c) optionally, an additive selected from the group consisting of plasticizers, adhesion promoters, suspending agents, pigments, effects pigments, colorants, optical brighteners, leveling agents, therapeutic agents, and combinations thereof. When applied to a bare nail surface and dried, the polish forms a film that may be peeled off the nail surface without use of a polish remover.

7 Claims, No Drawings

NON-AQUEOUS PEELABLE NAIL POLISH

TECHNICAL FIELD

This invention relates to peelable nail polish formulations.

BACKGROUND

Nail polishes, sometimes called nail lacquers, are aqueous or solvent-based compositions designed for application to the surface of a nail. After application, the coated nail is dried to remove the volatile liquid carrier, thereby forming a film on the nail surface. The film is typically removed by rubbing the film with a nail polish remover containing a solvent such as acetone or an ester.

SUMMARY

In one aspect, there is described a non-aqueous nail polish that includes (a) a film-forming resin and (b) an organic solvent, with the proviso that if the film-forming resin is a cellulose polymer or copolymer, the polish contains no greater than 5% by weight, based upon the weight of the polish, of the cellulosic polymer or copolymer. The polish forms a film that (a) has a Persoz hardness of 50-230 within 24 hours; (b) has a 60 degree gloss of at least 60 (preferably at least 80) after drying; (c) has an elongation to break of at least 50% after drying; (d) has a tensile modulus of at least 100 Mpa after drying; and (e) may be peeled off a bare nail surface following drying without use of a polish remover.

As used herein, the term "copolymer" refers to a polymer having at least two different monomer-derived units.

In some embodiments, the non-aqueous nail polish may include an additive selected from the group consisting of plasticizers, suspending agents, pigments, effects pigments, colorants, optical brighteners, leveling agents, adhesion promoters, dimethicones, and combinations thereof. In some embodiments, the non-aqueous nail polish may include a therapeutic additive. The film-forming resin may be selected from the group consisting of polyvinyl butyral, vinyl acetate polymers and copolymers, vinyl alcohol polymers and copolymers, vinyl chloride polymers and copolymers, styrene copolymers, polyester polymers and copolymers, polyurethane polymers and copolymers, cellulosic polymers and copolymers, aldehyde resins, and alkyd resins, with the proviso that if the film-forming resin is a cellulosic polymer or copolymer, it is present in an amount no greater than 5% by weight, based upon the weight of the polish.

In some embodiments, the film-forming resin includes polyvinyl butyral, a vinyl chloride polymer or copolymer, or a vinyl acetate polymer or copolymer. In some embodiments, the non-aqueous nail polish is free from cellulosic polymers and copolymers.

In a second aspect, there is described a non-aqueous nail polish consisting of: (a) a film-forming resin selected from the group consisting of polyvinyl butyral, vinyl acetate polymers and copolymers, vinyl chloride polymers and copolymers, vinyl alcohol polymers and copolymers, and combinations thereof; (b) an organic solvent; and (c) optionally, an additive selected from the group consisting of plasticizers, suspending agents, pigments, effects pigments, colorants, optical brighteners, leveling agents, adhesion promoters, dimethicones, and combinations thereof. When applied to a bare nail surface and dried, the polish forms a film that may be peeled off the nail surface without use of a polish remover.

The non-aqueous nail polishes may be applied to a bare nail surface (i.e. without first applying a primer). When applied to a bare nail surface, the formulations dry to form a tough, flexible, film that adheres well to the nail, but can be peeled substantially intact from the nail surface without the use of nail polish remover.

The details of one or more embodiments of the invention are set forth in the description below. Other features, objects, and advantages of the invention will be apparent from the description and from the claims.

DETAILED DESCRIPTION

Non-aqueous nail polish formulations are described in the Summary of the Invention, above. The non-aqueous nail polish formulation includes one or more film-forming polymers. Examples include polyvinyl butyral, vinyl acetate polymers and copolymers, vinyl alcohol polymers and copolymers, vinyl chloride polymers and copolymers, styrene copolymers (e.g., styrene-butadiene copolymers, styrene-ethylene-butylene-styrene block copolymers, styrene-ethylene-propylene-styrene block copolymers, and the like), polyester polymers and copolymers, aldehyde resins, alkyd resins, and polyurethane polymers and copolymers. In general, the total amount of film-forming polymer is 6-65% by weight, based upon the total weight of the formulation. Preferably, the total amount is 15-45% by weight, more preferably 15-30% by weight. Cellulosic polymer and copolymers may be included in an amount no greater than 5% by weight, based upon the weight of the formulation.

The non-aqueous nail polish formulation may include one or more plasticizers. Preferably, the plasticizer is included in an amount no greater than 20% by weight, based upon the total weight of the formulation. In some embodiments, the amount of plasticizer is 2-15% by weight or, more preferably, 3-10% by weight, based upon the total weight of the formulation. Examples of suitable plasticizers include acetyltributylcitrate, tri-n-butyl citrate, castor oil, tribenzoin, camphor, sucrose benzoate, sucrose acetate isobutyrate, triphenyl phosphate, dibutyl phthalate, diethyl phthalate, trimethylpentanyl dibenzoate, trimethylpentanyl diisobutyrate, and N-ethyl o/p-toluenesulphonamide. Blends of plasticizers may also be used.

The non-aqueous nail polish formulation may include one or more colorants, dyes, pigments, and/or effects pigments (e.g., glitters, pearls, and micas) in an amount ranging from 1-20% by weight, preferably 2-15% by weight, based on the total weight of the formulations. Examples include titanium dioxide, Red #6 lake, Red #7 lake, Blue #1, Yellow #5, and the like.

The non-aqueous nail polish formulation may include one or more suspending agents. Preferably, the suspending agent is included in an amount between 0.1 and 5% by weight, preferably between 0.5 and 3% by weight, and more preferably between 1 and 2.5% by weight, based upon the total weight of the formulation. Examples of suitable suspending agents include stearalkonium hectorite clays, stearalkonium bentonite clays, silicas, and the like.

The non-aqueous nail polish formulation may include additives such as optical brighteners, leveling agents, dimethicones, benzophenone-1, adhesion promoters, and the like. Examples of other suitable additives include therapeutically effective additives such as biocides, bactericides, fungicides, antibiotics, moisturizers, humectants, vitamins, proteases, bleaching compounds (e.g., hydrogen peroxide), antibodies, peptides, peptide conditioners, steroids, silver and silver-based compounds, antiviral compounds, and the like. In general, when present the additive is included in an amount no greater than 10% by weight, preferably no greater than 5% by weight, based upon the total weight of the formulation. For example, the additive may be present in an amount between 1 and 3% by weight, based on the total weight of the formulation.

The non-aqueous nail polish formulation includes one or more organic solvents. The organic solvent evaporates upon drying to leave a film over the nail. The organic solvent is included in an amount ranging from 10-90% by weight, based on the total weight of the formulation. Preferably, the amount of organic solvent is 40-80% by weight and, more preferably, 55-70% by weight, based on the total weight of the formulation. Examples of suitable organic solvents include alkyl acetate esters (e.g., methyl acetate, ethyl acetate, butyl acetate, propyl acetate, isobutyl acetate, and the like), aliphatic ketones (e.g., acetone, methyl ethyl ketone, and the like), and aliphatic alcohols (e.g., methanol, ethanol, propanol, butanol, isopropanol, and the like). Combinations of organic solvents may be used as well.

The formulations, following application, exhibit a dry time of 1-8 minutes, preferably 3-5 minutes, at 25° C., 50% relative humidity. The dried films preferably have the following properties:
 (a) Gloss (60 degree) (ASTM D-523): >60, preferably >80;
 (b) 24-hr Pendulum hardness (Persoz, secs) (ASTM D-4366): 50-230, preferably 100-150;
 (c) Elongation to break (%) (ASTM D-638): >50, preferably >75;
 (d) Tensile Modulus (MPa) (ASTM D-638): >100, preferably >200.

Example 1

A nail polish having the following ingredients was prepared (all percentages are weight percentages):
 Ethyl Acetate: 27%
 Butyl Acetate: 48%
 Methyl ethyl ketone: 7%
 Acetone: 7%
 Vinnol 40/50 (vinyl chloride-vinyl chloride copolymer; Wacker Chemie AG): 6%
 Bentone B27V Clay: 2%.
The nail polish dried to form a film after 4.1 minutes. The film had a Persoz hardness after 24 hours of 225 sec and a 60 degree gloss of 83.8.

Example 2

A nail polish having the following ingredients was prepared (all percentages are weight percentages):
 Methyl ethyl ketone: 27%
 Acetone: 27%
 Ethyl acetate: 5%
 Butyl acetate: 13%
 Vinnol 40/50 (vinyl chloride-vinyl acetate copolymer; Wacker Chemie AG): 23%
 Nitrocellulose: 2%
 Isopropanol: 1%
 Bentone B27V Clay: 2%.
The nail polish dried to form a film after 2.04 minutes. The film had a Persoz hardness after 24 hours of 191 sec and a 60 degree gloss of 84.5.

Example 3

A nail polish having the following ingredients was prepared (all percentages are weight percentages):
 Solbin M5 in methyl ethyl ketone (vinyl chloride-vinyl acetate copolymer; Shin-Etsu MicroSci, Inc.): 15%
 Bentone B27V Clay: 2%
 Methyl ethyl ketone: 58%
 Butyl acetate: 12%
 Ethyl acetate: 5%
 Nitrocellulose: 2%
 Isopropanol: 1%
 Uniplex 84 (acetyl tri-butyl citrate; Rein Chemie): 5%.
The nail polish dried to form a film after 1.22 minutes. The film had a Persoz hardness after 24 hours of 187 sec and a 60 degree gloss of 79.9.

Example 4

A nail polish having the following ingredients was prepared (all percentages are weight percentages):
 Butyl acetate: 54.7%
 Methyl ethyl ketone: 15.6%
 Polytex NX55 (tosylamide resin; Estron Chemical): 2.7%
 Butvar B79 (polyvinyl butyral; Eastman Chemical): 2.0%
 Vinnol 40/50 (vinyl chloride-vinyl acetate copolymer; Wacker Chemie AG): 4.8%
 Acetone: 5.6%
 Acetyl tributyl citrate: 7.0%
 Bentone B27V Clay: 1.2%
 Ethyl acetate: 3.8%
 Nitrocellulose: 1.9%
 Isopropanol: 0.8%.
The nail polish dried to form a film after 7.37 minutes. The film had a Persoz hardness after 24 hours of 65 sec and a 60 degree gloss of 63.8.

Example 5

A nail polish having the following ingredients was prepared (all percentages are weight percentages):
 Butyl acetate: 54.7%
 Methyl ethyl ketone: 10.0%
 Polytex NX55 (tosylamide resin; Estron Chemical): 2.7%
 Butvar B79 (polyvinyl butyral; Eastman Chemical): 2.0%
 Solbin C5R (vinyl chloride-vinyl acetate copolymer; Shin-Etsu MicroSci, Inc.): 16.0%
 Acetyl tributyl citrate: 7.0%
 Bentone B27V Clay: 1.2%
 Ethyl acetate: 3.8%
 Nitrocellulose: 1.9%
 Isopropanol: 0.8%.
The nail polish dried to form a film after 6.42 minutes. The film had a Persoz hardness after 24 hours of 72 sec and a 60 degree gloss of 64.7.

Example 6

A nail polish having the following ingredients was prepared (all percentages are weight percentages):
 Solbin M5 in methyl ethyl ketone (vinyl chloride-vinyl acetate copolymer; Shin-Etsu MicroSci, Inc.): 17.75%
 Methyl ethyl ketone: 26.63%
 Butyl acetate: 13.03%
 Ethyl acetate: 31.59%
 Nitrocellulose: 2.42%

Isopropanol: 1.04%
Stearalkonium Hectorite: 1.55%
Uniplex 84 (acetyl tri-butyl citrate; Rein Chemie): 6.00%.

The nail polish dried to form a film after 2.00 minutes. The film had a Persoz hardness after 24 hours of 101 sec and a 60 degree gloss of 85.3. The dried film also had an elongation to break of about 72% and a tensile modulus of about 300 mPa tested according to ASTM D-638 (average of 4 samples).

Example 7

A nail polish having the following ingredients was prepared (all percentages are weight percentages):
Solbin C5R (vinyl chloride-vinyl acetate copolymer; Shin-Etsu MicroSci, Inc.): 25.00%
Butyl acetate: 28.20%
Methyl ethyl ketone: 30.00%
Sucrose acetate isobutyrate: 9.00%
Stearalkonium Hectorite: 1.22%
Ethyl acetate: 3.88%
Nitrocellulose: 1.89%
Isopropanol: 0.81%.

The nail polish dried to form a film after 2.45 minutes. The film had a Persoz hardness after 24 hours of 81 sec and a 60 degree gloss of 92.3.

Note: In Examples 1-7, Vinnol 40/50, Bentone 27 Clay Gel, Solbin M5, and Solbin C5R are provided as solvent-containing dispersions or solutions. The weight percentages set forth above separate the solvent and resin/clay contents.

A number of embodiments of the invention have been described. Nevertheless, it will be understood that various modifications may be made without departing from the spirit and scope of the invention. Accordingly, other embodiments are within the scope of the following claims.

What is claimed is:

1. A non-aqueous nail polish consisting of:
   (a) a film-forming resin selected from the group consisting of vinyl acetate polymers and copolymers, vinyl alcohol polymers and copolymers, vinyl chloride polymers and copolymers, no greater than 5% by weight, based upon the weight of the polish, cellulosic polymers, and combinations thereof;
   (b) one or more organic solvents; and
   (c) optionally, an additive selected from the group consisting of plasticizers, adhesion promoters, suspending agents, pigments, effects pigments, colorants, optical brighteners, leveling agents, therapeutically effective agents, and combinations thereof,
   wherein when applied to a bare nail surface and dried, the polish forms a film that may be peeled off the nail surface without use of a polish remover.

2. The non-aqueous nail polish of claim 1 wherein the polish forms a film that (i) has a Persoz hardness of 50-230 seconds within 24 hours of drying, (ii) has a 60 degree gloss of at least 60 after drying, (iii) has a tensile modulus of at least 100 MPa after drying, and (iv) has an elongation to break of at least 50% after drying.

3. The non-aqueous nail polish of claim 1 wherein the film-forming resin is a vinyl acetate polymer or copolymer.

4. The non-aqueous nail polish of claim 1 wherein the film-forming resin is a vinyl chloride polymer or copolymer.

5. The non-aqueous nail polish of claim 1 wherein the polish is free from cellulosic polymers and copolymers.

6. The non-aqueous nail polish of claim 1 wherein the polish has a 60 degree gloss of at least 80 after drying.

7. A method of coating a nail comprising applying the non-aqueous nail polish of claim 1 to a bare nail surface to form a coated nail and drying the coated nail to form a peelable film on the nail surface.

* * * * *